United States Patent [19]
Stock et al.

[11] Patent Number: 6,030,977
[45] Date of Patent: Feb. 29, 2000

[54] FUNGICIDE SALTS

[75] Inventors: David Stock, Cambridge; Geoffrey Gower Briggs, Harpenden; Donald James Simpson, Haverhill, all of United Kingdom

[73] Assignee: Agrevo UK Limited, United Kingdom

[21] Appl. No.: 09/171,865

[22] PCT Filed: Apr. 25, 1997

[86] PCT No.: PCT/GB97/01141

§ 371 Date: Oct. 27, 1998

§ 102(e) Date: Oct. 27, 1998

[87] PCT Pub. No.: WO97/40682

PCT Pub. Date: Nov. 6, 1997

[30] Foreign Application Priority Data

Apr. 27, 1996 [GB] United Kingdom .................. 9608771

[51] Int. Cl.[7] ................... C07D 239/48; A01N 41/04; A01N 43/54; A01N 37/10; A01N 37/02
[52] U.S. Cl. ........................ 514/275; 514/161; 544/330
[58] Field of Search .................... 544/330; 514/275, 514/161

[56] References Cited

FOREIGN PATENT DOCUMENTS

| 0269916 | 6/1988 | European Pat. Off. . |
| 0642735 | 3/1995 | European Pat. Off. . |
| 92/19104 | 11/1992 | WIPO . |

OTHER PUBLICATIONS

P. Leroux, "Influence du pH, d'acides amines et de diverss substances organiques sur la fongitoxicite du pyrimethanil ( . . . ) vis–a–vis de certaines souches de Botrytis cinerea", Agronomie, vol. 14, 1994, pp. 541–554.

*Primary Examiner*—Richard L. Raymond
*Attorney, Agent, or Firm*—Ostrolenk, Faber, Gerb & Soffen, LLP

[57] ABSTRACT

Combining pyrimethanil with an organic acid having a volatility of less than 2 Pa at 20° C. results in a product which has valuable physical and biological properties.

12 Claims, No Drawings

FUNGICIDE SALTS

This application is a 371 of PCT/GB97/01141, filed Apr. 25, 1997.

This invention relates to compounds having fungicidal activity.

Pyrimethanil is a known fungicide, having the chemical name, 2-anilino-4,6-dimethylpyrimidine. However it has a relatively high vapour pressure which restricts it use. We have found that combining pyrimethanil with certain acids confers certain advantages to the compound.

According to the invention there is provided a product obtained by combining pyrimethanil with an organic acid, selected from long chain fatty acids, such as oleic acid and palmitic acid, saccharin, sulfonic acids, such as camphorsulfonic acid, salicylic acid and jasmonic acid.

It is generally preferred that the acid is present in at least a stoichiometric amount and in this case a salt is usually formed between pyrimethanil and the acid. Excess acid may be an advantage, e.g. in a molar ratio of acid to pyrimethanil of up to 2:1.

Certain salts of pyrimethanil are novel and useful and the invention also includes salts of pyrimethanil with an organic acid having a volatility of less than 2 Pa at 20° C.

As stated above one advantage of the products of the invention in particular is that they have a reduced vapour pressure compared with the free pyrimethanil, which increases the persistence of the compound on the crop to be protected from fungal attack. The reduced volatility also reduces levels of fungicide in the atmosphere.

In many cases the products have reduced phytotoxicity to certain plants.

In some cases the salts have increased activity compared with the free pyrimethanil. Another advantage is that the products have physical and chemical properties, which often make them amenable to provide better formulations than the free pyrimethanil. For example, the product of pyrimethanil with oleic acid is liquid which provides formulation advantages compared with the free pyrimethanil, which is a solid.

The products are useful in combating diseases for which pyrimethanil may be used e.g. Botrytis spp., especially *B. cinerea*, Venturia spp, Altenaria spp., and *Monolinia fructigena*. However the salt may also extend the useful activity to diseases such as mildews and particularly cereal powdery mildew (*Erysiphe graminis*) and glume blotch (*Leptosphaeria nodorum*).

The invention is illustrated in the following Examples.

EXAMPLE 1

A solution of pyrimethanil (1.0 g), toluene (50 ml) and oleic acid (1.42 g) was allowed to stand overnight at room temperature. The toluene was evaporated under reduced pressure to give pyrimethanil oleate, as an oil. (compound 1) nmr data:

| CDCl3 δ scale | |
| --- | --- |
| 0.9 | (3H, t, CH3) |
| 1.25 –1.42 | (20H, m, 10 × CH2) |
| 1.62 –1.76 | (2H, m, CH2) |
| 1.95 –2.1 | (4H, m, 2 × CH2) |
| 2.34 –2.42 | (8H, m, 2 × CH3, CH2) |
| 5.3 –5.42 | (2H, m, CH=CH) |
| 6.47 | (1H, s, pyrimidine CH) |
| 7.0 | (1H, t, ArH) |
| 7.32 | (2H, t, ArH) |
| 7.72 | (2H, d, ArH) |
| 8.67 | (1H, brs, NH) |

EXAMPLE 2

A solution of camphorsulfonic acid (1.25 g) in ethanol (10 ml) was added slowly to a solution of pyrimethanil (1 g) in toluene (20 ml) and the mixture allowed to stand for 30 minutes at room temperature. The mixture was evaporated under reduced pressure and the residue recrystallised from a mixture of diisopropyl ether and ethyl acetate to give pyrimethanil camphorsulfonate, m.p. 1 66–7° C. (compound 2)

In a similar way there was obtained
a) pyrimethanil saccharinate, m.p. 164–5° C. (compound 3)
b) pyrimethanil 7-trifluoromethylsaccharinate, m.p. 233–5° C. (compound 4)
c) pyrimethanil 4,7-dimethoxysaccharinate, m.p. 187–8° C. (compound 5)
d) pyrimethanil 4-chloro-7-methoxysaccharinate, m.p. 244–6° C. (compound 6)
e) pyrimethanil p-toluenesulfonate, m.p. 200–2° C. (compound 7)
f) pyrimethanil 2H-1-benzopyran-3-carboxylate, m.p. 126–7° C. (compound 8)
g) pyrimethanil phenoxyacetate, m.p. 76–8° C. (compound 9)
h) pyrimethanil phenylphosphonate, m.p. 126–8° C. (compound 10)
i) dipyrimethanil malonate, m.p. 126–8° C. (compound 11)
j) dipyrimethanil phthalate, m.p. 144–6° C. (compound 12)
k) pyrimethanil hydrogen phthalate, m. p. 149–51° C. (compound 13)

EXAMPLE 3

This Example illustrates relative persistence of the products of the invention compared with the free anilinopyrimidine.

Droplets (5×4 μl) of toluene solutions of radiolabelled pyrimethanil (0.05% w/v) were applied to microscope cover slips (13 mm diameter), which were positioned in Petri dishes. To some of the samples were added various fatty acids in molar ratios of pyrimethanil to acid of 1:1 and 1:2. The Petri dishes were left in a controlled environment room (20° C., 16 hours daylight) and after two days, slips were removed to determine how much pyrimethanil remained. This was done by transferring the slips to scintillation vials, each containing 10 ml of a dioxane based scintillation cocktail and measuring the amount of radiation by liquid scintillation counting. The results are as follows:

TABLE 1

Surface recovery of pyrimethanil after 2 days

| Compound | Surface recovery (%) |
| --- | --- |
| Pyrimethanil + oleic acid (1:1 molar) | 59.5 |
| Pyrimethanil + oleic acid (1:2 molar) | 77.9 |
| Pyrimethanil + lauric acid (1:1 molar) | 66.9 |

TABLE 1-continued

Surface recovery of pyrimethanil after 2 days

| Compound | Surface recovery (%) |
| --- | --- |
| Pyrimethanil + lauric acid (1:2 molar) | 80.1 |
| Pyrimethanil + myristic acid (1:1 molar) | 71.9 |
| Pyrimethanil + myristic acid (1:2 molar) | 63.3 |
| Pyrimethanil + palmitic acid (1:1 molar) | 61.6 |
| Pyrimethanil + palmitic acid (1:2 molar) | 71.5 |
| Pyrimethanil | 3.1 |

In a similar manner the example was repeated by adding saccharin to the pyrimethanil in the amounts shown (% w/v of the toluene solutions). Surface recovery measurements were made after 2 and 8 days The results are as follows:

TABLE 2

Surface recovery of pyrimethanil after 2 days

| Compound | Surface recovery (%) |
| --- | --- |
| Pyrimethanil + saccharin (0.05%) | 57.9 |
| Pyrimethanil (0.05%) + saccharin (0.1%) | 90.3 |
| Pyrimethanil (0.05%) + saccharin (0.2%) | 95.8 |
| Pyrimethanil (0.05%) | 2.0 |

TABLE 3

Surface recovery of pyrimethanil after 8 days

| Compound | Surface recovery (%) |
| --- | --- |
| Pyrimethanil (0.05%) + saccharin (0.05%) | 43.6 |
| Pyrimethanil (0.05%) + saccharin (0.1%) | 80.0 |
| Pyrimethanil (0.05%) + saccharin (0.2%) | 94.0 |
| Pyrimethanil (0.05%) | 1.1 |

It will be seen that the addition of the various acids increases the persistence of the pyrimethanil.

The compounds of Examples 1 and 2 also demonstrate greater levels of persistence than the free pyrimethanil.

EXAMPLE 4

5% Wettable powder formulations of compounds were diluted with water to the desired concentration and spayed over wheat test plants. One day later the plants parts were inoculated with appropriate test pathogens and kept under controlled environment conditions suitable for maintaining plant growth and development of the disease. After an appropriate time, the degree of infection of the plant was visually estimated. Five replicates were used for each dose of test compound. The results are as follows. The rates of a.i. (active ingredient) in the tables are based on free pyrimethanil.

a) *Botrytis cinerea* (assessed 7 days after inoculation)

| | % Control of disease at | |
| --- | --- | --- |
| Compound No | 5 g ai/hl | 2 g ai/hl |
| 5 | 94.4 | 85.4 |
| 6 | 94.4 | 88.7 |
| 7 | 91.0 | 83.1 |
| 8 | 93.2 | 84.2 |
| 9 | 90.4 | 75.2 |
| 10 | 94.4 | 87.6 |
| 12 | 91.0 | 77.5 |
| pyrimethanil (5% WP) | 85.4 | 75.2 |
| SCALA | 78.6 | 55.0 |

SCALA is the commercial 40% SC formulation of pyrimethanil b) *Erysiphe graminis* f. sp. *tritici* (assessed 7 days after inoculation)

| | % Control of disease at | |
| --- | --- | --- |
| Compound No | 100 g ai/ha | 25 g ai/ha |
| 4 | 39.7 | 15.5 |
| 8 | 75.9 | 27.6 |
| 12 | 51.7 | 3.4 |
| pyrimethanil (5% WP) | 27.6 | 3.4 |
| SCALA | 0 | 15.5 | c) *Leptosphaeria nodorum* (assessed 21 days after inoculation)

| | % Control of disease at | |
| --- | --- | --- |
| Compound No | 100 g ai/ha | 25 g ai/ha |
| 5 | 32.8 | 15.2 |
| 7 | 22.2 | 15.2 |
| 8 | 36.4 | 25.8 |
| 12 | 39.9 | 15.2 |
| pyrimethanil (5% WP) | 11.6 | 1.0 |
| SCALA | 15.2 | 11.6 |

We claim:

1. A product obtained by combining pyrimethanil with an organic acid, selected from long chain fatty acids, saccharin, sulfonic acids, salicylic acid and jasmonic acid.

2. Salts of pyrimethanil with an organic acid having a volatility of less than 2 Pa at 20° C.

3. A product according to claim 1 in which the acid is oleic acid.

4. A salt according to claim 2 in which the acid is oleic acid.

5. A fungicidal composition which comprises a product or salt as claimed in claim 1 in admixture with an agriculturally acceptable diluent or carrier.

6. A fungicidal composition which comprises a product or salt as claimed in claim 2, in admixture with an agriculturally acceptable diluent or carrier.

7. A fungicidal composition which comprises a product or salt as claimed in claim 3, in admixture with an agriculturally acceptable diluent or carrier.

8. A fungicidal composition which comprises a product or salt as claimed in claim 4, in admixture with an agriculturally acceptable diluent or carrier.

9. A method of combating phytopathogenic fungi, at a locus infested or liable to be infested therewith, which comprises applying to the locus a a product or salt as claimed in claim 1.

10. A method of combating phytopathogenic fungi, at a locus infested or liable to be infested therewith, which comprises applying to the locus a product or salt as claimed in claim 2.

11. A method of combating phytopathogenic fungi, at a locus infested or liable to be infested therewith, which comprises applying to the locus a product or salt as claimed in claim 3.

12. A method of combating phytopathogenic fungi, at a locus infested or liable to be infested therewith, which comprises applying to the locus a product or salt as claimed in claim 4.

* * * * *